US00PP07877P

United States Patent [19]

Hillis

[11] Patent Number: Plant 7,877

[45] Date of Patent: Jun. 2, 1992

[54] HIBISCUS PLANT 'HILLIS VARIEGATED'

[76] Inventor: Harold B. Hillis, Rte. 2. Box 142, McMinnville, Tenn. 37110

[21] Appl. No.: 595,255

[22] Filed: Oct. 9, 1990

[51] Int. Cl.[5] ..... A01H 5/00
[52] U.S. Cl. ..... Plt./54
[58] Field of Search ..... Plt./54

*Primary Examiner*—James R. Feyrer

*Attorney, Agent, or Firm*—Klarquist, Sparkman, Campbell, Leigh & Whinston

[57] ABSTRACT

A novel *Hibiscus paeoniflorus L.* plant characterized by the combination of its variegated leaves; showy candy-striped bloom buds; semi-double flower form; excellent pot habit; good flower production; ease of rooting cuttings; flower life of two days; medium-sized leaves, mostly three lobed with rounded teeth or notches; and durability as a landscape subject.

2 Drawing Sheets

This invention relates to a new and distinct variety of hibiscus of the species botanically known as *Hibiscus paeoniflorus L.* I have selected "Hillis Variegated" as the varietal name for my new variety.

I originally noticed my new variety growing as one distinctive flowering branch on the parent cultivar growing in a cultivated area and more specifically in a nursery row at Hillis Nursery Company, Inc., Warren County, Tenn. This branch was particularly characterized and distinctive from the parent plant by its medium-sized variegated leaves which were variably shaped and three-lobed with notches, showy candy-striped blooms, semi-double flower form, good flower production, and a flower life of two days. The plant also demonstrated an ease of propagation by root cuttings, excellent pot habit, and durability in direct sunlight. The parent cultivar is *Althea paeoniflorus L.* I believed that the branch of my new variety that I first noticed on the parent plant was a limb sport of the parent plant.

Observation of these distinct features of the limb sport convinced me that it represented a new and distinct variety of hibiscus. The new cultivar was first asexually reproduced by taking softwood vegetative cuttings from the originally observed branch of the parent cultivar. Observation of this limb sport and continued observation and testing of progeny thereof, subsequently asexually propagated under my direction at Hillis Nursery Company by vegetative cuttings, has confirmed my observation that the selection comprises a new and distinct variety of hibiscus. In addition, horticultural examinations of successive generations of asexually propagated plants has repeatedly shown that the unique combination of characteristics displayed by my new variety are fixed and retained through successive generations of asexual reproduction.

Accordingly, I am convinced that my new plant represents a new and improved variety of *Hibiscus paeoniflorus L.*, as evidenced by the following unique combination of characteristics which have proven firmly fixed and which distinguish it from all other varieties of this species:

(1) Variegated leaves;
(2) Showy candy-striped bloom buds; and
(3) Semi-double flower.

The accompanying photographs depict the color and foliage of my new variety as nearly true as is reasonably possible in a color illustration of this character.

FIG. 1 is a color photograph of the present invention grown as a finished pot plant.

FIG. 2. is a color photograph illustrating the distinctive characteristics of the flower and variegated leaves of the present invention, compared with the flower and leaves of the parent cultivar.

FIG. 3 is a color photograph showing the variation in leaf shape that can be found on any single plant, and typical patterns of variegation.

FIG. 4 is a color photograph showing the colorful, candy-striped bloom bud of the present invention.

FIG. 5 is a color photograph showing bloom buds and a flower of the present invention.

One of the primary distinguishing characteristics of my new variety of hibiscus over other hibiscus varieties in the variegation of the leaves and the characteristically variable leaf shape. FIG. 2 best illustrates the variegation typical of my new variety. The variegated plant shown on the left of the photograph is the plant of the present invention, whereas the non-variegated plant on the right is the parent cultivar.

The characteristically variable leaf shape displayed by the present invention is best shown in FIG. 3. It may be noted that there is variability in the shape of the leaves of the new selection within any single plant.

The parent cultivar, *Althea paeoniflorus L.*, is believed by the inventor to be the most similar cultivar. The variegated leaves of the present invention particularly characterize "Hillis Variegated" from the parent cultivar (FIG. 2); in all other respects the two plants are similar insofar as has been observed as of this time.

The following is a detailed description of my new variety of *Hibiscus paeoniflorus L.*, with color terminology in accordance with The Royal Horticultural Society Colour Chart (hereinafter R.H.S.), published by The Royal Horticultural Society of London, England. The phenotype of the present invention may vary with changes in environmental conditions and factors such as light intensity and temperature; the plant has not been observed under all possible environmental conditions. The following phenotypic description is of a plant of the present invention grown in an outdoor container at Hillis Nursery Company, Inc., Warren County, Tenn. These characteristics have been repeatedly observed in asexually reproduced generations grown at Hillis Nursery in Warren County:

Parentage: A limb sport of *Althea paeoniflorus L.* Parent plant has no known varietal name.

Propagation: Relatively easy to propagate; holds to distinguishing characteristics when propagated using vegetative cuttings.

Classification:

1. *Botanical.—Hibiscus paeoniflorus L.*
2. *Commercial.*—Landscape or patio pot plant.

Plant

*Size.*—Mature plant size undetermined. Three year old plants average 3-4 feet when grown outdoors in zone 5.

*Vigor.*—Approximately 25 percent less than parent.

Foliage:

1. *Arrangement.*—Alternate.
2. *Shape.*—Juvenile; palmate, variable, but mostly with three lobes. Mature; palmate variable but mostly with three lobes with rounded teeth or notches.
3. *Leaf color.*—a. Major central portion of upper surface of mature leaves: Green, R.H.S. 138A-138B. b. Margin and portion of upper surface of mature leaves: Yellow, R.H.S. 160A-160B. c. Random blotches appearing at the interface between the major central portion of upper surface of mature leaves and the margin portion of upper surface of mature leaves: Green, R.H.S. 139C-139D.
4. *Apex.*—Acute to acuminate
5. *Base.*—Obtuse
6. *Surface texture.*—glabrous
7. *Leaf size.*—Medium; petiole base to apex approximately 7 to 7.5 cm.; and width, at widest point, approximately 4.5 to 5.0 cm.
9. *Petiole.*—Length 1.0 to 1.5 cm., pubescent.
8. *Petide Color.*—Green, R.H.S. 137B.
10. *Stipules.*—None.

Stems: Aspect smooth, slightly pubescent, becoming woody with age.

Plant habit: Semi-compact, irregularly upright.

1. *Breaking action.*—Good.
2. *Rooting.*—Good.
3. *Growth regulator.*—None required.
4. *Low light bud initiation.*—Good.
5. *Durability.*—Durable in direct sunlight as a potted patio plant or landscape subject, excellent pot habit.

Flower:

1. *Size.*—Medium, 6.0 cm.
2. *Borne.*—Axils of leaves, one per node.
3. *Form.*—Semi-doulbe.
4. *Life.*—Two days.
5. *Fragrance.*—None.

6. *Blooming habit.*—Good flower production; blooms continuously during growing season, June through August; blossoms 10 days after buds form.

Corolla:

1. *Texture.*—Smooth.
2. *Substnace.*—Medium thick.
3. *Shape.*—Variable.
4. *Color (fully open).*—a. Upper and Lower Surfaces: Pale Pink, R.H.S. 56D. b. Base of Petals: Dark Red, R.H.S. 59B.

Bud:

1. *Color.*—a. Red, R.H.S. 58A. b. Stripes: Pink, R.H.S. 62A-62B.
2. *Length.*—3.0 cm. average, one day before opening.

Calyx:

1. *Shape.*—Cup shaped, five pointed lobes, variegated, membranous.
2. *Length.*—1.5 cm.
3. *Color.*—Green, R.H.S. 138A-138B with yellow variegation, R.H.S. 160A-160B.

Epicalyx:

1. *Shape.*—Six to eight pointed, narrow, sword-shaped bracts.
2. *Length.*—0.5-1.0 cm.
3. *Color.*—Green, R.H.S. 138A-138B with yellow variegation, R.H.S. 160A-160B.

Peduncle:

1. *Length.*—0.5-1.0 cm.
2. *Strength.*—Medium.
3. *Aspect.*—Smooth, slightly pubescent.
4. *Color.*—Green, R.H.S. 138A-138B.

Reproductive organs:

1. *Androecium.*—a. Anthers: Numerous, some petaloid. b. Filaments: Length 1.0-2.0 cm. c. Pollen: (1) Medium (2) Color *Pale yellow, R.H.S.* 4D. d. Staminal column: 50% petaloid upper, 50% smooth. (1) Length: 1.0-2.0 cm. (2) Color: White, lower.
2. *Gynocium.*—a. Stigma: 5 in number, rounded, discoid, hairy. b. Color: White.
3. *Ovary.*—Cylindrical, elongate. a. Color: Pale Green, R.H.S. 4D.

Seed formation: Does not set seeds.

I claim:

1. A new and distinct variety of *Hibiscus paeoniflorus L.*, substantially as herein shown and described, and characterized particularly as to novelty by the combination of its variegated leaves; showy candy-striped bloom buds; and semi-double flower form.

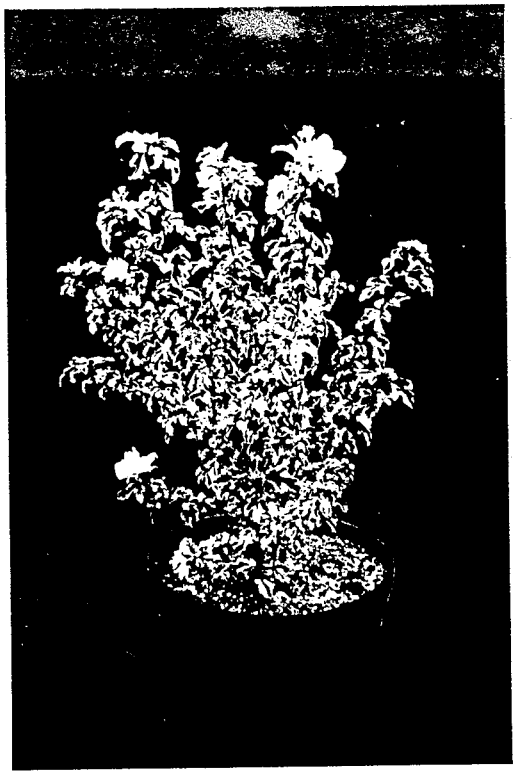
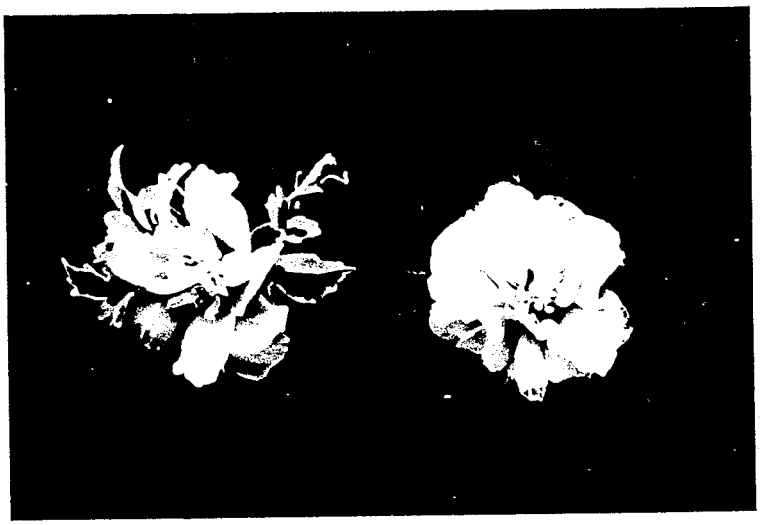

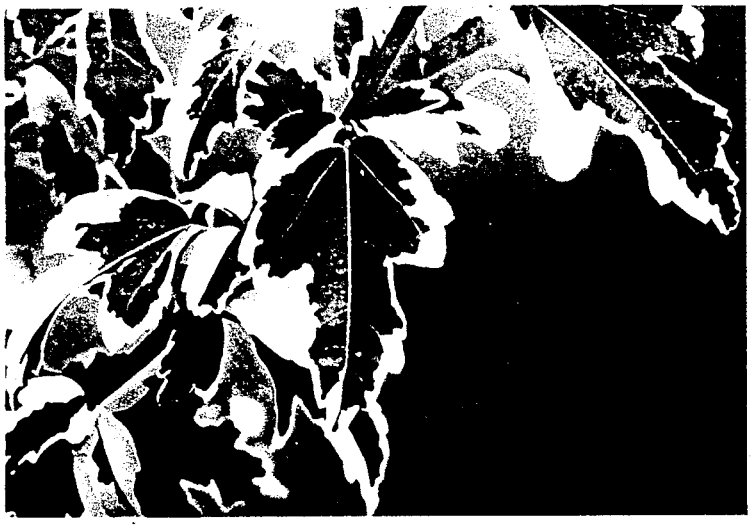
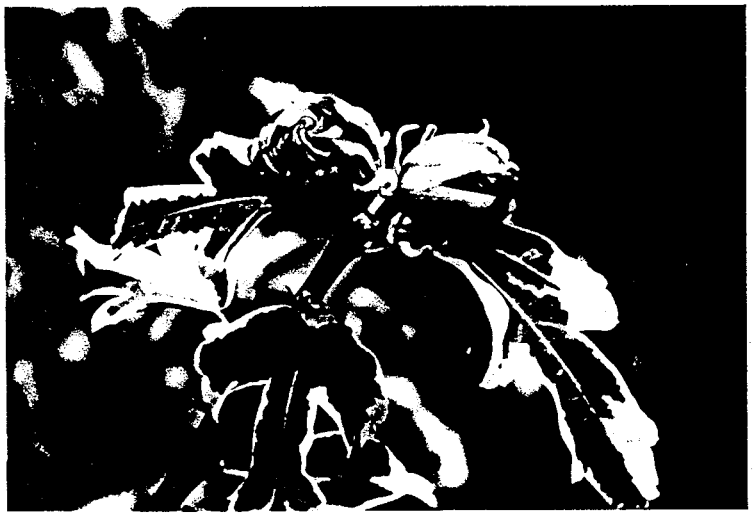
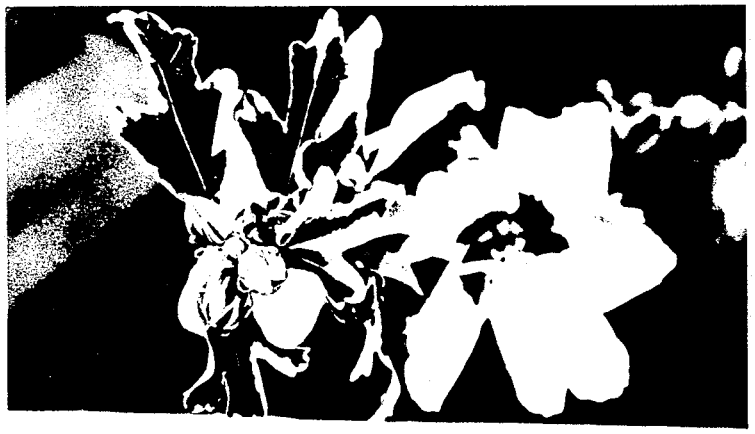

* * * * *